(12) United States Patent
Sykora

(10) Patent No.: US 10,585,040 B2
(45) Date of Patent: Mar. 10, 2020

(54) ATR REFLECTION ELEMENT AND ATR SPECTROSCOPY METHOD

(71) Applicant: Lorenz Sykora, Ismaning (DE)

(72) Inventor: Lorenz Sykora, Ismaning (DE)

( * ) Notice: Subject to any disclaimer, the term of this patent is extended or adjusted under 35 U.S.C. 154(b) by 170 days.

(21) Appl. No.: 15/760,005

(22) PCT Filed: Sep. 8, 2016

(86) PCT No.: PCT/EP2016/071211
§ 371 (c)(1),
(2) Date: Sep. 18, 2018

(87) PCT Pub. No.: WO2017/045998
PCT Pub. Date: Mar. 23, 2017

(65) Prior Publication Data
US 2019/0011364 A1    Jan. 10, 2019

(30) Foreign Application Priority Data
Sep. 14, 2015   (DE) .................. 10 2015 011 687

(51) Int. Cl.
*G01J 3/00*     (2006.01)
*G01N 21/552*   (2014.01)
(Continued)

(52) U.S. Cl.
CPC ......... *G01N 21/552* (2013.01); *A61B 5/1455* (2013.01); *G01J 3/14* (2013.01); *G01N 21/3577* (2013.01); *G01N 2021/3595* (2013.01)

(58) Field of Classification Search
CPC ............. G01N 21/552; G01N 21/3577; G01N 2021/3595; G01N 21/45; G01N 15/06;
(Continued)

(56) References Cited

U.S. PATENT DOCUMENTS

| 6,128,091 A | 10/2000 | Uchida et al. |
| 7,200,311 B1 | 4/2007 | Han |
| 2004/0199060 A1* | 10/2004 | Oshima ............... A61B 5/14532 600/310 |

FOREIGN PATENT DOCUMENTS

| DE | 10 2004 045 902 B4 | 8/2006 |
| EP | 1 308 714 A1 | 5/2003 |

(Continued)

OTHER PUBLICATIONS

International Search Report for Application No. PCT/EP2016/071211 dated Jan. 12, 2016, 3 pages.
(Continued)

*Primary Examiner* — Abdullahi Nur
(74) *Attorney, Agent, or Firm* — Seed Intellectual Property Law Group LLP

(57) ABSTRACT

An ATR reflection element includes a main body with a first effective refractive index n1, a transmission layer which comprises a first layer boundary, and an opposite second layer boundary. The transmission layer takes up a fluid by way of the second layer boundary, wherein the transmission layer adjoins the main body. The boundary between the transmission layer and the main body is formed by the first layer boundary, wherein the transmission layer at the second layer boundary has a second effective refractive index n2. The first effective refractive index n1 is greater than the second effective refractive index n2 and the second effective refractive index n2 is greater than 1, wherein the first effective refractive index n1 and the second effective refractive index n2 are determined in each case in a vacuum at 25° C. at the IR wavelength $\lambda_{ATR}$, wherein $\lambda_{ATR}$ is selected from the wavelength range between 2 μm and 20 μm. Further- (Continued)

more, the disclosure relates to an ATR spectrometer comprising said ATR reflection element, and an ATR spectroscopy method.

34 Claims, 6 Drawing Sheets

(51) Int. Cl.
*A61B 5/1455* (2006.01)
*G01J 3/14* (2006.01)
*G01N 21/3577* (2014.01)
*G01N 21/35* (2014.01)

(58) Field of Classification Search
CPC . G01J 3/14; A61B 5/1455; A61B 5/00; G02B 1/11; B05D 1/00
See application file for complete search history.

(56) References Cited

FOREIGN PATENT DOCUMENTS

EP          1 998 163 A1    12/2008
WO          02/18919 A1     3/2002

OTHER PUBLICATIONS

Schumacher, H., et al. "Applications of Microstructured Silicon Wafers as Internal Reflection Elements in Attenuated Total Reflection Fourier Transform Infrared Spectroscopy," Applied Spectroscopy, vol. 64, No. 9, Sep. 1, 2010, pp. 1022-1027.

* cited by examiner

ATR REFLECTION ELEMENT AND ATR SPECTROSCOPY METHOD

BACKGROUND

Technical Field

The disclosure relates to an ATR reflection element for reinforcing the absorption signal in ATR-IR spectroscopy, an ATR spectrometer with the ATR reflection element, an ATR spectroscopy method and a production method for said ATR reflection element.

Description of the Related Art

Attenuated total reflection infrared spectroscopy, referred to below in abbreviated form as ATR, is an established, widely-used method for analyzing analytes and fluid, in particular largely non-translucent substances, in other words, those substances that hinder or prevent standard transmission measurement.

ATR spectrometers and structures for infrared spectroscopy regularly use so-called ATR reflection elements. These must, in accordance with the physical effects on which they are based, have a higher refractive index for the radiation used than the medium to be tested. The ATR reflection elements usually have surface regions for coupling and surface regions for decoupling the radiation used. Furthermore, they have surface regions for the contact with the medium to be tested. The total reflection occurs on the latter surface regions. The ATR reflection elements can here be designed as single or multiple reflection elements.

ATR reflection elements are produced from materials with a high refractive index for the radiation used. Typically, zinc selenide, diamond, thallium bromide-iodide, amorphous material transmitting infrared radiation (AMTIR), germanium or silicon are used.

Alongside the above ATR reflection element, ATR spectrometers regularly have a radiation source, e.g., an infrared laser and/or black body radiator (glow wire), and a detector for the reflected radiation with downstream electronics for the visualization, processing and evaluation of the measurements.

The broad area of application of infrared spectroscopy demands the development of increasingly more efficient ATR reflection elements. In general, a larger quantity of reflections leads to a stronger absorption signal, although the radiation may not be so far attenuated that the signal-to-noise ratio prevents an analysis of the signal. Depending on the material used for the ATR reflection element, it is therefore also advantageous to keep the optical passage through the ATR reflection element as short as possible in order to reduce the absorption of the radiation in the ATR reflection element itself. At the same time, achieving a high absorption by the medium with a comparatively short radiation passage is one of the great challenges when developing new ATR reflection elements.

In DE 10 2004 045 902 B4, a thin, transparent layer with a high refractive index is arranged on a substrate with a lower refractive index in order to shorten the optical passage length. Via the substrate, the radiation is coupled into the thin layer. In said thin layer, the radiation experiences multiple total reflection on the boundaries to the medium to be tested and to the substrate. Due to the low thickness of the layer, the optical passage is kept short through the ATR reflection element, despite the large number of reflections.

The subject of U.S. Pat. No. 6,128,091A is a reflection element for measuring blood components, e.g., measuring blood sugar. For this purpose, so-called projections are arranged on the surface, which are intended to improve the contact, for example with the lip of the test person, and enable a penetration of the saliva between the reflection element and the lip. In one embodiment, the reflection element is designed as a triple reflection element.

The compromise between the number of reflections and the optical passage length is the determining property in the design of ATR reflection elements, in particular when testing weakly absorbing samples. A higher signal-to-noise ratio improves the precision of the measurement and shortens the necessary measuring time considerably.

SUMMARY AND INITIAL DESCRIPTION

Embodiments of the present disclosure improve the signal-to-noise ratio and thus efficiency compared to standard ATR reflection elements, in particular when measuring weakly absorbing samples.

For example, described herein is an ATR reflection element, in particular an ATR-IR reflection element, comprising a main body with a first effective refractive index, a transmission layer, whereby the transmission layer comprises an, in particular flat, first layer boundary and an opposite second layer boundary, preferably parallel to the first layer boundary, wherein the transmission layer is designed and configured to take up a fluid by way of the second layer boundary, in particular wherein the second layer boundary is permeable for a fluid, wherein the transmission layer adjoins the main body, in particular a first boundary surface region of the main body, wherein the boundary between transmission layer and the main body is formed by the first layer boundary, wherein the transmission layer has a second effective refractive index at the second layer boundary, wherein the first effective refractive index is greater than the second effective refractive index and the second effective refractive index is greater than 1. The first effective refractive index and the second effective refractive index are each to be determined in a vacuum at 25° C. at the wavelength $\lambda_{ATR}$, wherein $\lambda_{ATR}$ is selected from the wavelength range 2 µm to 20 µm. The ATR reflection element thus fulfils the above properties for at least one wavelength of said wavelength range. In an advantageous design, the properties for all wavelengths of the wavelength range from 2 µm to 20 µm are fulfilled.

Without being bound to the above descriptions, the results observed for the first design of the disclosure, in particular the unexpectedly clear strengthening of the measuring signal, are combined with the following possible mechanism. If a fluid is applied onto the transmission layer, in particular the measurement layer, this penetrates said transmission layer through the second layer boundary. Electromagnetic radiation which penetrates into the transmission layer from out of the main body during the measurement procedure experiences transmission by the fluid and/or by analytes, which have been brought in to the transmission layer with the fluid when running through the transmission layer. Portions of the electromagnetic radiation are with the above transmission absorbed in accordance with the excited states of the fluid or in accordance with the excited states of the analytes contained in the fluid, wherein this absorption contributes to the measurement signal. The analyte or analytes are those substances contained in a sample or the fluid, via which a statement should be made during the measurement, i.e., in particular, molecules or molecule mixtures of their absorption spectrum should be determined. It is also feasible for the fluid to be removed before the measurement, and only the analyte or analytes to be tested remain. For example, a fluid containing an analyte can be used, wherein the fluid evaporates prior to the measurement. In this case, the transmission of electromagnetic radiation during the measurement is achieved only by the analytes within the transmission layer. Naturally, the fluid itself, such as a gas, can also be the subject of the measurement. On the second layer boundary, a total reflection of the electromagnetic radiation occurs, wherein an absorption of the electromagnetic radiation occurs through the interaction of the evanescent wave with the fluid and/or the analytes beyond the second layer boundary. Thus, with total reflection, an absorption of electromagnetic radiation occurs analogously to standard ATR reflection elements. The additional surprising absorption described above during transmission via the fluid and/or through the taken-up analytes leads to a considerable strengthening of the absorption signal compared to standard ATR reflection elements, which are based solely on an absorption during total reflection. It is therefore assumed that the technical effect is based on a surprising combination of absorption during transmission and absorption during total reflection of light.

Usually, the first boundary surface region runs parallel to the first layer boundary. The first describes the corresponding side region of the main body, while the latter refers to the boundary to the transmission layer, which adjoins the first boundary surface region. The transmission layer thus lies in contact on the first boundary surface region, or adjoins said boundary surface region. A boundary surface region in the sense of the present disclosure is a boundary surface of the main body, and thus determines its expansion and form in connection with other boundary surface regions of the main body. Preferably, the different boundary surface regions of the main body are flat and in particular connected.

IR radiation in the sense of the present disclosure is electromagnetic radiation with a wavelength in the wavelength range of 780 nm to 1 mm, wherein preferably, the wavelength area of 2 to 20 µm is meant. Light in the sense of the present disclosure should be equated with electromagnetic radiation. Light or electromagnetic radiation is preferably understood to be IR radiation, in particular in the wavelength range of 2 to 20 µm.

A transmission layer in the sense of the present disclosure is a layer through which electromagnetic radiation, preferably IR radiation, IR radiation in the wavelength range of 2 to 20 µm particularly preferred, can be at least proportionately or predominantly transmitted. Typical essential IR-transparent materials, which for example can form a transmission layer, are sufficiently known. Preferably, this is a transmission layer in the sense of the present disclosure when with a layer thickness of 1 mm and an irradiation of light along the surface normals of a boundary surface or surface of the transmission layer, the majority portion, in particular at least 50%, preferably at least 75%, of the IR light of a wavelength of 2 µm and/or 20 µm is transmitted during a measurement in the vacuum.

It has been shown to be advantageous to establish boundary surface regions for coupling and decoupling the used electromagnetic radiation in order to reduce reflection losses of the light or its radiation when entering the ATR reflection element. These can comprise the same boundary surface region or be arranged spaced apart from each other. In one design, two boundary surface regions are provided for coupling and third boundary surface regions are provided for decoupling, wherein these are preferably spaced apart from each other. However, it is also feasible that second boundary region areas are provided for coupling and decoupling. In one embodiment variant, the minimum distance between the second and third boundary region areas is greater than the respective maximum expansion of the second and third boundary region area. It is also preferred when said second and third boundary region areas are inclined in different directions, in particular with a view onto a plane that is orthogonal to the second layer boundary. In particular, it is preferred when the second and third boundary surface regions are planar, so that mathematical planes can be assigned to them, wherein these planes preferably run together and intersect on the side of the second layer boundary on which the main body is to be found.

In particular, it is preferred when the ATR reflection element has at least one second boundary surface region of the main body for coupling electromagnetic radiation and at least one third boundary surface region of the main body for decoupling electromagnetic radiation, these preferably being arranged opposite the transmission layer and/or the first boundary surface region.

In a further embodiment, the second and third boundary surface regions are arranged parallel, particularly preferred within the same mathematical plane. In a further design, the second and third boundary surface regions are not arranged parallel, but have deviating inclinations. The latter design enables a more effective prevention of total reflection when radiation exits from the ATR reflection element on the third boundary surface regions.

In one advantageous embodiment, the first and second layer boundaries are arranged parallel, in particular are designed in a plane-parallel manner. This facilitates the calculation of the beam passage and ensures even incidence, refractive and reflection angles. It has also been shown that, in this case, the efficiency of total reflection is higher on the second layer boundary.

The transmission layer that is enclosed by the first and second layer boundaries is characterized in one preferred embodiment by the fact that it has at least one cross-sectional area parallel and/or at least one cross-sectional area orthogonal to the first and/or second layer boundary, which in particular has a plurality of alternately solid regions and hollow regions open towards the second layer boundary.

Preferably, the hollow regions of the at least one cross-sectional area are open orthogonally to the first and/or second layer boundary to said second layer boundary. The opening of the hollow regions towards the second layer boundary enables a penetration of a fluid into said hollow regions via the second layer boundary. The solid and hollow regions in the cross-sectional areas form volumes in the three-dimensional space which can be described as three-dimensional, solid first structural elements or as three-dimensional hollow first structural elements that are open towards the second layer boundary.

Preferably, at least one cross-sectional area parallel to the two layer boundaries has solid regions, and hollow regions that are open towards the second layer boundary at regular average spacing, in particular, periodical average spacing. Preferably, a fluid can enter into said hollow regions via the second layer boundary, and be absorbed into the transmission layer.

Accordingly, in a further development of the ATR reflection elements according to the disclosure, it is provided that the transmission layer comprises or is formed of a plurality of solid first structural elements spaced apart from one another and/or a plurality of hollow first structural elements spaced apart from one another open towards the second layer boundary.

Furthermore, it can be provided that the hollow to the second layer boundary and/or solid first structural elements of the transmission layer are arranged periodically or aperiodically, in particular periodically, preferably such that at least one cross-sectional area, in particular a plurality of cross-sectional areas, is arranged between the first and second layer boundary, in particular parallel to and spaced apart from the first and second layer boundary, wherein said cross-sectional area comprises similarly formed, solid regions of the solid first structural elements arranged periodically or aperiodically, in particular periodically, and/or hollow open regions of the hollow first structural element open towards the second layer boundary, in particular wherein these solid and hollow open regions are arranged alternately. If the solid and/or hollow first structural elements, in particular the solid structural elements and the hollow first structural elements open to the second layer boundary, are smaller in their expansion and their average spacing parallel to the first and/or second layer boundary, for example than a used measuring wavelength, in particular an IR wavelength, they form a so-called subwavelength structure (SWS), also known as a submeasurement wavelength structure, since the wavelength used for the measurement specifies the subwavelength structure. The transmission layer in the sense of the present disclosure is thus preferably a layer containing subwavelength structures, in particular subwavelength structures for wavelengths of ≥20 μm, preferably of ≥2 μm. These are also referred to as an SWS layer. If the expansion and average spacing of the solid and/or hollow first structural elements that are open to the second layer boundary are larger in all spatial directions than the measurement wavelength used, they do not form a subwavelength structure (SWS) for this wavelength. In this case, the light or the electromagnetic radiation can dissolve the individual solid and the hollow first structural elements that are open to the second layer boundary, so that an effective refractive index is not created, but different refractive indexes are present for successive structural elements. Accordingly, a subwavelength structure (SWS) is present as a or in the transmission layer for the development of an effective refractive index on the layer boundaries, in other words, here, the transmission layer comprises the solid and/or the hollow first structural elements that are open to the second layer boundary, which form a subwavelength structure (SWS).

It has been shown to be advantageous when the solid and/or hollow regions open towards the second layer boundary are arranged periodically, i.e., in a two-dimensional Bravais lattice. An alternative embodiment comprises aperiodically arranged solid and/or hollow regions open towards the second layer boundary, in particular porous structures formed from said aperiodically arranged solid and/or hollow first structural elements open towards the second layer boundary.

The first and second effective refractive index in the sense of the present disclosure are the refraction indices that are experienced by the light of the measurement wavelength, in particular IR wavelength $\lambda_{ATR}$, wherein $\lambda_{ATR}$ is preferably selected from a wavelength range of 2 to 20 μm. These effective refractive indices can for example result from material mixtures of two materials with two different refractive indices. For example, it is also feasible to produce a porous material structure, e.g., a porous silicon structure, wherein the first or second effective refractive index does not result solely from the silicon, but also from the porous hollow spaces and the vacuum that they may contain (with 25° C. and the wavelength $\lambda_{ATR}$). Grooves or columns in a material can also influence the effective refractive index. If the average spacing of the solid first structural elements, for example with columns, or the average spacing of the first structural elements that are open towards the second layer boundary, such as with holes, are however multiple times larger than for example a measurement wavelength of 5 μm, for the intermediate spaces and the columns, different effective refractive indices result, so that the layer boundary cannot be assigned a refractive index as a whole.

Preferably, with the present disclosure, only one, in particular second, effective refractive index occurs respectively on the overall first layer boundary and/or on the overall second layer boundary. An effective refractive index in the sense of the present disclosure is—unless explicitly specified otherwise—to be determined at 25° C. and in a vacuum in the absence of a fluid. A person skilled in the art can easily ascertain whether the refractive index is an effective refractive index for a specified wavelength, by irradiating a light beam, in particular a laser light beam of said wavelength into the body. With the second layer boundary, the irradiation occurs when determining the respective effective refractive index, in particular the effective second refractive index, preferably at an angle of 70°, particularly preferred below 45°, to said layer boundary. If this light beam is curved in different directions, regions are present in the body or in the transmission layer with different refractions. If the light beam is only curved in one direction, the body has an effective refractive index, which can be determined experimentally under the above conditions. An effective refractive index is thus wavelength related, for example, the first and second refractive index is related to a wavelength from the wavelength range 2 to 20 μm. Preferably, this is determined at 15 μm, in particular 10 μm, preferably 5 μm and particularly preferred, 2 μm.

Preferably, the solid first structural elements are designed in the form of, in particular even, raised portions, in particular in the form of columns, blocks or longitudinal ridges and/or the hollow first structural elements that are open towards the second layer boundary are designed in the form of, in particular identical, wells, preferably of recesses, holes or grooves. Naturally, a transmission layer can also comprise mixtures of the designs described above of the solid and/or hollow first structural elements facing towards the second layer boundary, or be formed from these. In particular in the case of the aperiodical arrangement of the first structural elements, porous solid and/or hollow first structural elements facing towards the second layer boundary are provided.

The solid and/or hollow first structural elements facing towards the second layer boundary can have a wide range of different geometric forms. Preferred are embodiments of the elevations and wells, in particular columns and/or holes and/or blocks and/or grooves, with essentially square, rectangular, round or polygonal cross-sectional areas in at least one direction, in particular parallel or orthogonal to the second layer boundary. The solid first structural elements can essentially also comprise cylinders and/or cuboids and/or cubes and/or cones and/or cone stumps and/or pyramids and/or pyramid stumps and/or spherical segments and/or spherical layers and/or spherical discs. Grooves and/or longitudinal elevations of a wide range of different profiles are also feasible for hollow and/or solid structural elements. It is preferred when said cross-sectional areas of the individual solid and/or hollow structural elements facing towards the second layer boundary essentially correlate in at least one direction, in particular parallel or orthogonal to the second layer boundary, in particular within the scope of production-related deviations.

Columns in the sense of the present disclosure are structural elements with a larger longitudinal extension than width, wherein the longitudinal extension is preferably at least double as long, in particular at least five times as long, as the width. The determined profile parallel to the first and/or second layer boundary of an individual column is preferably round, polygonal or square.

Particularly preferred are solid and/or hollow first structural elements facing towards the second layer boundary, in particular columns, cubes, cuboids or grooves that have an average height or average depth that is larger, in particular multiple times larger, than the average space apart between adjacent solid first structural elements or between adjacent hollow first structural elements facing towards the second layer boundary, in particular between adjacent columns or between adjacent holes or grooves. Particularly preferred are also solid and/or hollow first structural elements, in particular columns, holes or grooves, that have a maximum height or maximum depth that is larger than, in particular multiple times larger, than the minimal space apart between adjacent solid and/or hollow first structural elements facing towards the second layer boundary, in particular between adjacent columns or between adjacent holes or grooves. Preferably, in one embodiment, multiple times should be understood such that the height or depth is at least three times, at least five times or at least ten times larger than the average space apart. The determination of the heights of the solid first structural elements and depths of the hollow first structural elements facing towards the second layer boundary of the transmission layer is preferably conducted orthogonally to the first and/or second layer boundary. The height of the columns or the depth of the grooves is in particular determined orthogonally to the first and/or second layer boundary. Here, the average space apart between two solid first structural elements is average minimal space apart between the opposite outer surfaces or the opposite sections of the outer surfaces of said first structural elements (i.e., the width of the intermediate space). For the hollow first structural elements the same applies accordingly with regard to the inner surfaces.

In contrast to the average distance, the average spacing in the sense of the present disclosure is the average distance after which the solid and/or hollow first structural elements facing towards the second layer boundary repeat themselves. It should be noted that these are fundamentally always spacings between solid structural elements or spacings between hollow structural elements. Spacings between a hollow and an adjacent solid structural element are not what is meant. In this sense, the spacing between adjacent hollow and/or solid structural elements should be designed as the spacing between respective adjacent solid structural elements or the spacing between adjacent hollow structural elements respectively or however the spacing between adjacent solid structural elements respectively and the spacing between adjacent hollow structural elements respectively, but not as the spacing between a hollow structural element to the adjacent solid structural element. In the case of periodically arranged hollow and/or solid first structural elements, the average spacing corresponds to the so-called lattice constant in the corresponding spatial direction. Accordingly, it is not generally the measurement of the respective solid and/or hollow first structural elements that is decisive for the average spacing, but the distance of the respective closest, in particular identical, first structural elements. With space-filling solid and/or hollow first structural elements, the average distance can be very small and the average spacing relatively large. With solid first structural elements formed as cylinders or hollow first structural elements facing towards the second layer boundary designed as cylindrical holes, the average spacing for example corresponds to the average distance between the axes of rotation of adjacent cylinders or cylindrical holes. If for example two columns have a respective radius of 1 µm and a diameter of 2 µm, and the distance between the axes of rotation is 2.5 µm, the average spacing of the two columns is 2.5 µm and the average distance of said columns is 0.5 µm. With first structural elements with identical forms, the expansion and the average distance of the first structural elements are usually smaller than the average spacing of the first structural elements. Thus, for the characterization of submeasurement wavelength structures (SWS), the average spacing of the first structural elements is the decisive value. With one- or two-dimensional objects, in particular with parallel layer boundaries, a differentiation between the average distance and the average spacing overall is not necessary, since the values are identical (the outer surfaces coincide with the object itself).

The lattice constants, as is known, are the length specifications required to describe the smallest unit of a lattice, in particular an elementary cell. Since here, for periodically arranged solid and/or hollow first structural elements facing towards the second layer boundary, an essentially two-dimensional lattice is described (structuring of a boundary region), the lattice constants usually comprise two length specifications and an angle, preferably of 90° or 60°. In the case of grooves arranged in parallel, however, the lattice that is arranged on the two-dimensional surface is one-dimensional. In particular, it is preferred when the two longitudinal specifications are identical, i.e., two lattice constants are identical. With straight, periodically occurring parallel grooves or elevations, one lattice constant is sufficient to describe the periodical arrangement of the structural elements, which corresponds to the average spacing between the grooves or elevations, and which is determined orthogonally to the course of the grooves or elevations. The lattice constant of a structural element in the sense of the present disclosure corresponds to the lattice constant that can be assigned to the lattice of the periodical arrangement of said structural element. With columns, for example, the respective position of the axes of rotation is decisive. With parallel, straight grooves, the lattice constant corresponds to the spacing of the grooves, measured orthogonally to the longitudinal alignment of the grooves. Aperiodically arranged structural elements do not have a lattice constant. With periodical solid and/or hollow first structural elements facing towards the second layer boundary, the average spacing preferably corresponds to at least one lattice constant, in particular a Bravais lattice constant, i.e., the lattice constant of a Bravais lattice.

In one possible design, the solid and/or hollow first structural elements facing towards the second layer boundary, in particular the solid first structural elements in the form of elevations, have one first outer surface respectively, a second outer surface orthogonal to it and a third outer surface opposite the first outer surface, which is also preferably arranged orthogonally to the second outer surface. Here, it can preferably be provided that the first and third outer surface is curved. Preferably, by contrast, the second outer surface is flat, in particular plane-parallel to and/or parallel to the second layer boundary. In a further possible design, the solid first structural elements are cylindrical columns respectively.

In one suitable embodiment, at least one lattice constant, in particular at least one Bravais lattice constant, preferably all lattice constants, of the periodically arranged solid and/or hollow first structural elements facing towards the second layer boundary and/or the average spacing of the periodically and aperiodically arranged solid and/or hollow first structural elements facing towards the second layer boundary fulfil the condition (1a)

$$p_{max} < \frac{500\ \mu m}{n_1},$$

preferably the condition (1b)

$$p_{max} < \frac{250\ \mu m}{n_1},$$

particularly preferably, the condition (1c)

$$p_{max} < \frac{100\ \mu m}{n_1},$$

wherein $n_1$ is the first effective refractive index. Preferably, all lattice constants of the periodic solid and/or hollow first structural elements facing towards the second layer boundary fulfil the correlation 1a, in particular 1b, and particularly preferred 1c. In the sense of the present disclosure, $p_{max}$ is the value that is assigned to the lattice constant and/or to the average spacing.

In a further preferred embodiment, the solid and/or hollow first structural elements facing towards the second layer boundary have lattice constants and/or average spacings of $p_{max} \geq 0.1$ µm, particularly preferably lattice constants and/or average spacings with $p_{max} \geq 0.4$ µm, in particular lattice constants and/or average spacings of $p_{max} \geq 0.7$ µm. In a further preferred embodiment, the solid and/or hollow first structural elements facing towards the second layer boundary have lattice constants or average spacings with $p_{max} \leq 4$ µm, particularly preferably, lattice constants and/or average spacings with $p_{max} \leq 2$ µm, in particular lattice constants and/or average spacings with $p_{max} \leq 1.3$ µm. In a very particularly preferred design, the solid and/or hollow first structural elements facing towards the second layer boundary have lattice constants and/or average spacings of 0.1 µm$\leq p_{max}$ 4 µm, particularly preferred, lattice constants and/or average spacings of 0.4 µm$\leq p_{max} \leq 2$ µm, in particular, lattice constants and/or average spacings of 0.7 µm$\leq p_{max} \leq 1.3$ µm. These average spacings and/or lattice constants also permit measurements in the short-wave infrared range. Additionally, over average spacings of this size, a filter effect can also be achieved. If particles of different sizes are present in the fluid, with a suitable design of the hollow regions of the transmission layer, a penetration into said transmission layer only of particles up to a certain size can be enabled. Only these are then subject to the transmission, and thus contribute more strongly to the absorption signal than the components remaining over the transmission layer. The cellular portions of human blood have different sizes, for example. Human leucocytes have an average diameter of 7 to 20 µm, human erythrocytes have an average diameter of 6 to 8 µm, and human thrombocytes have an average diameter of just 1.5 to 3 µm. As described above, the average spacings of the hollow regions of the transmission layer can be designed such that only erythrocytes and thrombocytes or only thrombocytes together with the blood serum or also only the blood serum can penetrate into the transmission layer and are subject to transmission. As a result, the standard upstream separation of the blood into its constituent parts is no longer required. In particular, a selective IR measurement of specific analytes is possible under suitable conditions, wherein preferably, impurities do not enter into the measurement signal, or if so, only with reduced intensity.

Accordingly, the ATR reflection element according to the disclosure and the ATR spectrometer according to the disclosure, in which respectively the second layer boundary of the transmission layer comprise or represent a sample take-up area with the generic use of the ATR reflection element or the ATR spectrometer, can be used for the in particular direct measurement of solid analytes contained in fluids. Here, it can be provided that the ATR reflection element according to the disclosure and the ATR spectrometer according to the disclosure, in which respectively the second layer boundary of the transmission layer comprise or represent a sample take-up area with the generic use of the ATR reflection element or the ATR spectrometer can be used not only for measuring analytes that have penetrated into the transmission layer or are present, but also for separating the solid analytes with different diameters present in fluids, as applied with the fluid onto the transmission layer as a sample take-up area. Only those analytes with a diameter that is smaller than the openings specified by the hollow first structural elements that are open towards the second layer boundary and/or is smaller than the intermediate spaces specified by the solid first structural elements, in the region of the second layer boundary of the transmission layer, penetrate into the transmission layer and can be used for a selective measurement.

Preferably, the transmission layer has an essentially constant second effective refractive index $n_2$ over its entire layer thickness.

In one embodiment, the fill factor of the transmission layer lies in the range of 1 to 85%, preferably in the range of 3 to 30%, and particularly preferably in the range of 10 to 20%. As a fill factor, the greater the volume of the transmission layer that is taken up by the solid regions and in correlation, the lower the volume of the transmission area that is taken up by the hollow regions. For the above regions, a considerable strengthening of the absorption signal can be determined, wherein simultaneously, the structural integrity is guaranteed.

Preferably, the transmission layer has an average thickness in the range of 0.1 to 50 µm, particularly preferably in the range of 1 to 20 µm, very particularly preferably in the range of 4 to 6 µm, wherein the average thickness is preferably determined orthogonally to the first layer boundary. In a particularly preferred manner, the average thickness corresponds to the average distance between the first and second layer boundary.

Preferred is an embodiment in which the solid and/or the hollow first structural elements open to the second layer boundary have at least two, in particular at least 20, essentially identical cross-sectional areas orthogonally to the first and/or second layer boundary. Further preferred is an embodiment in which the solid and/or the hollow first structural elements open to the second layer boundary have essentially at least one identical cross-sectional profile respectively parallel to the first and/or second layer boundary. In particular, it is preferred when the solid or the hollow first structural elements open to the second layer boundary are preferably essentially designed identically, i.e., within the scope of production and measurement precision, they have the same dimensions and forms.

In a further preferred embodiment, the main body and the solid first structural elements consist of one material, in particular are constructed in one piece. For example, the first structural elements can be grooves or columns which are formed in a silicon crystal.

If the transmission layer is applied to the main body, the solid regions of the transmission layer can also comprise materials other than those of the main body, preferably materials with a similar absorption behavior and/or similar refractive index. These are similar when the absorption coefficients and/or refractive index deviate from each other by not more than 30%, preferably by 15%.

Preferably, the ATR reflection element and/or the main body comprise a crystal, in particular a single crystal, or is formed by such a crystal.

In one advantageous embodiment, the ATR reflection element comprises silicon and/or germanium and/or zinc selenide and/or diamond and/or thallium bromide-iodide and/or AMTIR, in particular, consists of these. Preferably, the ATR reflection element comprises silicon, germanium, zinc selenide, diamond, thallium bromide-iodide or AMTIR, in particular, silicon, germanium or zinc selenide.

There are numerous options for the geometric design of the ATR reflection element. Preferably, the second and/or third boundary surface region of the main body for coupling and decoupling is not arranged on the side of the ATR reflection element on which the transmission layer is present, but in particular on the side that lies opposite the transmission layer.

In one advantageous embodiment, the second boundary surface region of the main body comprises two structural elements for coupling and/or the third boundary surface region comprises two structural elements for decoupling the electromagnetic radiation, in particular solid and/or open hollow second structural elements. A separate fourth boundary surface region, in particular for coupling and decoupling light, can also be provided, which comprises solid and/or open hollow second structural elements.

The determination of the height of the solid second structural elements and the depth of the hollow second structural elements is conducted orthogonally to the boundary surface region on which these structural elements are present.

Preferably, these solid and/or these hollow second structural elements are formed as periodical elevations and/or wells, particularly preferred as, in particular V-shaped, grooves or longitudinal elevations, in particular elevations that taper in the direction of the second layer boundary. Second structural elements preferably differ from the first structural elements described above in that the average distance and/or the average spacing between the solid structural elements, preferably elevations, in particular columns, cones or walls, is greater than with the first structural elements, preferably at least double the size, in particular at least five or ten times the size. Alternatively or additionally preferably, second structural elements differ from the first structural elements described above in that the average distance and/or the average spacing between the in particular open hollow structural elements, preferably recesses, in particular grooves or notches, is greater than with the hollow first structural elements that are open towards the second layer boundary, preferably at least double the size, in particular at least five times or ten times the size.

It should be noted that hollow structural elements are generally open in the sense of the present document. Open means that the affected hollow structural element does not have a closed hollow space, but this space is open, preferably open for taking up a fluid. This does not exclude the possibility that instead or in addition, for example, closed pores can also be present. Solid structural elements that are open are by contrast not present.

Hollow first and/or second structural elements in the sense of the present disclosure are not filled with material, i.e., they are characterized by the absence of material, in contrast to the solid first or second structural elements. Accordingly, hollow first and/or second structural elements, in particular wells, are only to be found delimited from areas that are filled with material. Said areas filled with material can for example be a solid continuous layer or solid adjacent first structural elements, in particular elevations, e.g., columns. In particular, it can be provided that the transmission layer, aside from the solid high structural elements, in particular wells, such as holes, is solid, wherein the solid areas are continuously connected to each other. These areas that are continuously connected to each other are not solid first structural elements, wherein said first structural elements are isolated and/or delimitable from each other. Equally, it is also feasible that solid and hollow first structural elements together represent or form the transmission layer. For example, a checkerboard pattern with square elevations and square wells bordering across corners are feasible. Further, grooves that are delimited from each other by walls or longitudinal elevations are feasible. The grooves in this case represent hollow open first structural elements and the longitudinal elevations represent solid first structural elements. Solid in the sense of the present disclosure means in particular the presence of material, while hollow means the absence of material. Preferably, the material here is the material from which the main body is formed.

Particularly preferred for the transmission layer are periodically arranged solid first structural elements, which extend from the first layer boundary to the second layer boundary, wherein between the solid first structural elements, a continuous, material-free area is present.

According to the disclosure, in one embodiment, a plurality of solid and/or hollow first structural elements that are open towards the second layer boundary are present on the ATR reflection element or in the transmission layer. Preferably, it is provided that at least 100, in particular at least 1,000, preferably at least 10,000, of these solid or hollow first structural elements that are open towards the second layer boundary are present on the ATR reflection element or in the transmission layer. Preferably, it is provided that at least 100, in particular at least 1,000, preferably at least 10,000, solid first structural elements are present in the form of elevations, in particular columns, on the ATR reflection element. In a further preferred embodiment, it is provided that at least 20, in particular at least 200, preferably at least 2,000, hollow first structural elements that are open towards the second layer boundary are present in the form of wells, in particular grooves, on the ATR reflection element.

The number of solid and/or hollow first structural elements that are open towards the second layer boundary, such as columns, of the transmission layer of the ATR reflection element, per surface, is preferably multiple times larger than the number of the solid and/or hollow second structural elements, such as grooves, as are present on the second and/or third and/or fourth boundary surface regions on the same surface. In one advantageous design, at least five times, in particular at least ten times, more first structural elements are present per surface in the transmission layer than second structural elements per surface on the second and/or third boundary surface regions of the ATR reflection element.

Preferably, the solid and/or hollow first structural elements that are open towards the second layer boundary are designated as fine structures with a first average spacing and the solid and/or the above-mentioned hollow second structural elements are designated as rough structures with a second average spacing, wherein the first average spacing is less than the second average spacing. The average spacings relate to the spacing of the solid structural elements to the adjacent solid structural elements or the spacing of the hollow structural elements to the adjacent hollow structural elements. In particular, it is preferred when the first average spacing is smaller by a factor of 5, in particular by a factor of 10, preferably by a factor of 100, than the second average spacing. Preferably, rough structures also have a greater depth than fine structures.

In one preferred embodiment, the lattice constant and/or the average spacing of the above-mentioned hollow and/or the solid second structural elements lies in the range of 30 to 3,000 μm, particularly preferred in the range of 100 to 1,000 μm, in particular in the range of 400 to 600 μm. With these distances an effective refractive index on a flat layer boundary towards the vacuum with a wavelength of 20 μm does not occur.

Preferably, the hollow and/or solid second structural elements, in contrast to the first structural elements, do not form submeasurement wavelength structures, in particular with regard to the wavelengths in the range of 2 to 20 μm, preferably 2 μm. It is preferred when these hollow and/or solid second structural elements also have no flat layer boundary with an effective refractive index, even when determining the refractive index with the above-mentioned wavelength range, in contrast with the first structural elements. To a far greater extent, each solid second structural element preferably has an effective refractive index at 2 μm and 25° C. in a vacuum, which while it can correlate with adjacent solid structural elements cannot however extend continuously beyond the distances, in particular hollow structural elements, between said solid second structural elements. If the boundary to the vacuum is assigned a third layer boundary, which results from the height of the second structural element, said third layer boundary has different refractive indices in different regions, preferably in such a manner that in several regions, the refractive index corresponds to that of the main body, and in other regions, the refractive index corresponds to that of the vacuum.

In a further preferred embodiment, main bodies and solid second structural elements consist of one material, in particular are constructed in one piece. For example, the hollow second structural elements can be grooves, in particular V-shaped grooves, which are formed in a silicon crystal, wherein the walls of the grooves represent the outer surface of adjacent solid structural elements that consist of silicon or are connected to the remaining silicon crystal of the main body as a single piece.

Further, it is particularly preferred when the solid and/or hollow first structural elements that are open towards the second layer boundary have steeper flanks, at least in sections, than the solid and/or aforementioned hollow first structural elements, wherein the inclination of the flanks relative to the boundary region area of the main body on which said first structural elements and/or second structural elements are present is to be determined. Here, the main surface is assigned an inclination of 0° and a flank orthogonal to it an inclination of 90°. Preferably, the transmission layer has solid and/or hollow first structural elements that are open towards the second layer boundary, which at least in sections have an inclination of 90°, i.e., they are orthogonally aligned to the first layer boundary or to the second boundary surface region, at least in sections. With the solid and/or hollow structural elements, it is preferred when the inclination is less than 60°, in particular less than 50°, preferably less than 37°, with regard to the boundary surface region of the main body below, in particular of the second and/or third boundary surface region of the main body below.

In one suitable embodiment, the ATR reflection element is designed as a single reflection element. In one alternative embodiment, the ATR reflection element is designed as a multiple reflection element. However, it has been shown that with the ATR reflection element according to the disclosure, often fewer reflections are required than with standard ATR reflection elements due to the higher absorption efficiency. Preferably, the ATR reflection element or the beam passage of the ATR reflection element during generic use is designed such that no more than five, in particular no more than four, preferably no more than three total reflections of a transmitted photon occur on the second layer boundary.

In a further preferred embodiment, wells of hollow second structural elements, in particular grooves, preferably essentially V-shaped grooves, have a depth in the range of 15 to 1,517 μm, particularly preferably a depth in the range of 50 to 500 μm, in particular a depth in the range of 100 to 200 μm.

The mask region is the regions of a boundary surface that are covered by the photo mask during a lithography step and are thus not exposed to light. In the sense of this disclosure, in particular those areas that have a boundary region equipped with solid and/or hollow structural elements, in which no elevations or wells are present, are regarded as being the mask region. These regions are then described as plateau regions and preferably correspond to the maximum height, in particular the maximum distance, from the main body. Preferably, the plateau regions are flat and/or parallel with the second layer boundary. The same applies to the solid and/or hollow first structural elements open to the second layer boundary. The surface or surface expansion of the mask region is, in a preferred embodiment, less than 50%, particularly preferably less than 5%, in particular 0% of the surface expansion of the boundary region equipped with the second structural elements, in particular, the second, third, and/or fourth boundary surface. In the case of the V-shaped grooves that are preferably used as hollow second structural elements, a mask range of 0% means that the rising flank of a V-shaped groove directly borders on the falling flank of the adjacent groove. As a result an even coupling and decoupling of the radiation used is achieved.

The object that forms the basis of the disclosure is further solved with an ATR spectrometer, comprising at least one ATR reflection element according to the disclosure.

Said ATR spectrometer comprises at least one light source, in particular at least one infrared light source, at least one detector, in particular designed and configured to detect infrared radiation, optical elements, in particular mirrors and/or lenses, for guiding the beam generated by the light source, and at least one ATR reflection element according to the disclosure as described above. Preferably, the light source is an infrared laser and/or a black body emitter (glow wire). Particularly suitable in connection with the first structural elements of the transmission layer are infrared lasers. According to the disclosure, the light source is arranged such that the light or at least a portion of the light hits the first layer boundary of the ATR reflection element below an angle $\alpha 1$.

Preferably, the second layer boundary, with the generic use, is the, in particular exposed, sample take-up area of the ATR spectrometer. Preferably, the first and second layer boundaries are arranged plane-parallel and the transmission layer of the ATR reflection element comprises the solid and/or hollow first structural elements that are open towards the second layer boundary, which are preferably periodically arranged.

In one suitable embodiment, the at least one lattice constant, in particular a Bravais lattice constant, preferably all lattice constants, and/or the average spacing between said solid and/or hollow first structural elements that are open towards the second layer boundary, fulfil the correlation (II)

$$p_{max} < \frac{\lambda_{ATR2}}{n_{1b}(1 + \sin\alpha_1)},$$

wherein $n_{1b}$ is a third effective refractive index of the main body of the ATR reflection element with light of wavelength $\lambda_{ATR2}$ and at 25° C. in a vacuum, $\alpha 1$ is the angle of incidence on the first layer boundary, and $\lambda_{ATR2}$ shows the wavelength used in said ATR spectrometer for measurement. In the sense of the present disclosure, $p_{max}$ is the value that is assigned to the lattice constant and/or the average spacing. Preferably, the wavelength $\lambda_{ATR2}$ used for measurement is the wavelength 15 μm, in particular 10 μm, preferably 5 μm, particularly preferred 2 μm. In one advantageous embodiment, a wavelength range of 20 μm to 2 μm fulfils this requirement. At 25° C. in a vacuum, the third effective refractive index $n_{1b}$ assumes the same value as the first effective refractive index $n_{1a}$ when the value of $\lambda_{ATR}$ and $\lambda_{ATR2}$ correlates.

In a further suitable embodiment, the at least one lattice constant, in particular a Bravais lattice constant, preferably all lattice constants, and/or the average spacing between these and the solid and/or hollow first structural elements that are open towards the second layer boundary fulfil the correlation (III)

$$p_{max} < \frac{\lambda_{ATR3}}{n_{1c}(1 + \sin\alpha_1)},$$

wherein $n_{1c}$ represents a fourth effective refractive index of the main body of the ATR reflection element, measured with wavelength $\lambda_{ATR3}$, at 25° C. and shown in a vacuum, $\alpha 1$ denotes the angle of incidence on the first layer boundary, and $\lambda_{ATR3}$ is the shortest wavelength used for measurement in said ATR spectrometer. In the sense of the present disclosure, $p_{max}$ is the value that is assigned to the lattice constant and/or the average spacing. At 25° C. in a vacuum, the third effective refractive index $n_{1b}$ assumes the same value as the fourth effective refractive index n1c when the value of $\lambda_{ATR2}$ and $\lambda_{ATR3}$ correlates. In general, the first, third and fourth effective refractive index of the main body differ only with regard to the wavelength used to determine the effective refractive index, wherein the measurement is conducted in each case in a vacuum at 25° C.

Preferably, it is provided that when the above correlations (II) and/or (III) for $p_{max}$ are fulfilled, the hollow and/or solid first structural elements represent subwavelength structures (SWS) with regard to said wavelengths $\lambda_{ATR2}$ and/or $\lambda_{ATR3}$. The transmission layer can therefore in this context also be described as the SWS transmission layer with regard to the affected wavelength.

The light source of the ATR spectrometer is preferably arranged such that the irradiation vector of the light, in particular the light beam, lies on one plane, which is oriented orthogonally to the first and/or second layer boundary and/or parallel to the V-shaped grooves, or such that the light is irradiated orthogonally to the second boundary surface region and/or is emitted orthogonally to the third boundary surface region, or is irradiated and/or emitted orthogonally to at least one surface region of the second structural elements, in particular orthogonally to at least one flank of each second structural element. The above arrangements have been shown to be particularly advantageous in order to enable controlled irradiation and at the same time to minimize light reflection during penetration into the main body or exiting from the main body.

In one particularly preferred embodiment variant, the transmission layer has only solid first structural elements, which are in particular arranged periodically. In particular, it is preferred when said solid first structural elements, in particular columns, are arranged on an area formed by the first layer boundary. Alternatively, it is also feasible that the transmission layer has only open hollow first structural elements, such as holes, in an otherwise continuous solid transmission layer.

In one suitable embodiment, the second structural elements are formed from solid and open hollow second structural elements in alternating sequence, in particular wherein these are grooves and the longitudinally extended elevation between the grooves. The light that enters in the SWS region is preferably not capable of dissolving solid and hollow areas. To a far greater extent, solid and hollow areas form a transmission layer with a fifth effective refractive index $n_{2b}$ on the second layer boundary with wavelength $\lambda_{ATR2}$, in particular $\lambda_{ATR3}$, at 25° C. and in a vacuum. This fifth effective refractive index of the second layer boundary can, depending on the form and design of the solid and/or hollow first structural elements that are open towards the second layer boundary, also be constant over the entire layer thickness, or only be present on the second layer boundary. The fifth effective refractive index $n_{2b}$ depends significantly on the refractive index of the solid regions of the SWS and on the fill factor of the transmission layer. On the second layer boundary, at 25° C. in a vacuum and measured with the same wavelength from the wavelength range of 2 μm to 20 μm, the fifth effective refractive index $n_{2b}$ assumes the value of the second effective refractive index $n_{2a}$. Preferably, the SWS are designed and installed in such a manner that the transmission layer has an essentially constant fifth effective refractive index $n_{2b}$ over its entire layer thickness. Said fifth effective refractive index is in particular smaller than the first effective refractive index $n_{1a}$ and/or the third effective refractive index $n_{2b}$ and/or the fourth effective refractive index $n_{1c}$. One surprising advantage of the use of the ATR reflection element according to the disclosure lies in the fact that the absorption signal of the sample to be measured is considerably strengthened. Here, it is assumed that the electromagnetic radiation alongside the attenuated total reflection that gives the ATR reflection elements their name also experiences absorption during transmission through the fluid that penetrates into the hollow regions of the transmission layer and/or through the analytes that penetrate into the hollow regions.

This results in a significance strengthening of the absorption signal compared to standard ATR reflection elements.

This strengthening of the absorption signal permits, e.g., the shortening of the optical passage length of the radiation through the ATR reflection element without leading to a loss of capacity. As a result, materials can also be used for the ATR reflection element that strongly absorb parts of the radiation used, which due to their chemical stability, their cost or the processing options are however otherwise highly suitable.

In the alternative embodiment, also named the second design of the disclosure, the transmission layer serves as a region for coupling and if necessary for decoupling the radiation. For this purpose, it is preferably designed in the form of the subwavelength structures already mentioned above. These give the boundary surface region fitted with the transmission layer anti-reflective properties and thus reduce reflection losses when electromagnetic radiation enters into the ATR reflection element, and thus increase the general signal strength. With this embodiment variant of the present disclosure, the sample take-up area can comprise the hollow and/or solid second structural elements and/or the solid and/or hollow first structural elements that are open towards the second layer boundary described above, wherein the ATR reflection element can for example be designed as a triple reflection element. According to the disclosure, it can also be provided that a first transmission layer constitutes the region for coupling the radiation, while a second transmission layer, in particular an opposite second transmission layer, constitutes the sample take-up area with generic use of the ATR reflection element. It has been shown that the so-called first design of the disclosure, in which the transmission layer forms the sample take-up area, attains the object that forms the basis of the disclosure in a far clearer manner than the so-called second design of the disclosure, in which the boundary surface region containing or formed from the hollow and/or solid second structural elements acts as a sample take-up area.

Advantages of the disclosure are further attained by an ATR spectroscopy method, wherein a beam, consisting of electromagnetic waves, in particular in the infrared range, is coupled into an ATR reflection element, in particular as described above, the light beam is decoupled from the ATR reflection element, and between coupling and decoupling, impinges at least once onto an in particular planar first layer boundary and penetrates into the transmission layer delimited by this layer boundary and capable of fluid take-up, wherein the beam of light undergoes refraction at the first layer boundary and, on passage through the transmission layer, undergoes transmission by the fluid taken up into the transmission layer, in particular containing at least one analyte, and on the fluid-permeable, planar, second layer boundary, wherein the beam of light undergoes total reflection at the second layer boundary, wherein the beam of light, on further passage through the transmission layer, again undergoes transmission by the fluid and/or analyte taken up into the transmission layer, wherein on transmission, the beam of light also undergoes absorption by the fluid, in particular by the analyte, wherein the beam of light once again enters the main body at the first layer boundary, and wherein the beam of light attenuated by the absorption is detected with a suitable detector after emerging from the ATR reflection element, in particular wherein the detected light beam is analyzed. The detector preferably converts electromagnetic radiation into electrical signals or comprises a device that is capable of doing so. Preferably, the passage through the transmission layer, as described above, is conducted more than once, as described above, in particular wherein the beam of light undergoes total reflection within the main body at least one before the beam of light exits and is detected by the detector.

The method can further comprise a step of sample dispensing, wherein a fluid, in particular containing analytes, is dispensed onto the transmission layer and penetrates into the transmission layer. The fluid can be a fluid to be analyzed or the analyte itself. Preferably, in one design of the method, the fluid is in particular evaporated with the addition of thermal energy, wherein analytes remain within and if appropriate also on the transmission layer.

The electromagnetic radiation, in particular radiation in the infrared range, is coupled into the ATR reflection element on the boundary surface regions, in particular on the second boundary surface regions, for coupling the electromagnetic radiation of the ATR reflection element. Said boundary surface regions, in particular the second boundary surface region of the main body for coupling the electromagnetic radiation, can comprise hollow and/or solid second structural elements or be formed from them. The electromagnetic radiation is here thus preferably coupled into the ATR reflection element in such a manner that at angle $\alpha 1$ it impinges on the first layer boundary with $$\sin^{-1}\left(\frac{n_3}{n_{1b}}\right) < a_1 < \sin^{-1}\left(\frac{n_{2c}}{n_{1b}}\right)$$

wherein $n_3$ is a sixth effective refractive index of the fluid and/or the analytes with a wavelength used $\lambda_{ATR2}$ and a measurement temperature, and wherein $n_{2c}$ is a seventh effective refractive index of the transmission layer with the fluid for the wavelength used $\lambda_{ATR2}$ on the first layer boundary, wherein $n_{2c}$ is significantly dependent on the refractive index of the solid areas of the SWS, the fill factor of the transmission layer and the sixth refractive index $n_3$ of the fluid and/or analytes. The seventh effective refractive index $n_2$ is thus determined in the presence of the fluid. Angles of incidence that fulfil this condition have been shown to be particularly suitable. The total reflection at the first layer boundary is regularly prevented when the above relations are maintained, and the total reflection is guaranteed on the second layer boundary of the transmission layer. The electromagnetic radiation is refracted during transfer from the main body into the transmission layer on the first layer boundary, and if necessary when passing through the transmission layer. Preferably, the beam passage in the main body and/or within the transmission layer is essentially linear. When passing through the transmission layer, the radiation is transmitted through the fluid located in the hollow regions of the transmission layer and/or through the analytes located in the hollow regions of the transmission layer. Here, absorption may occur. On the second layer boundary between the effective transmission layer and the fluid and/or analytes lying above it, the radiation is totally reflected. Subsequently, the radiation again passes through the transmission layer. At the first layer boundary, the radiation is finally refracted again into the main body. Depending on the embodiment of the ATR reflection element, the radiation can then either be coupled directly via the boundary surface region, in particular the third boundary surface region, for decoupling the electromagnetic radiation from the ATR reflection element, or again be guided into the transmission layer in order to again run through the transmission total reflection procedure. The latter procedure can also be repeated multiple times. The decoupled electromagnetic radiation is fed to the detector. With suitable data processing technology, the absorption spectrum is recorded in order to be subsequently processed and analyzed.

The subject of the disclosure is further a method for producing the ATR reflection element according to the disclosure, comprising the provision of an in particular flat, plane-parallel substrate, in particular a silicon wafer. The method further comprises the formation of a transmission layer with solid and/or hollow first structural elements that are open towards the second layer boundary.

This is achieved through
(1) application of at least one coating layer, in particular photoresist layer, onto a flat first area of the substrate, preferably the first boundary surface region of the main body of the later ATR reflection element.

For the further steps for forming the transmission layer with the solid and/or hollow first structural elements that are open towards the second layer boundary, preferably, a first etching method, a method with metal-assisted chemical etching (MACE) or a lift-off method can be provided. The first etching method, in particular a dry etching method, has been shown to be particularly suitable. This comprises the following steps:
(2a) machining by use of lithography, in particular DUV lithography, of the first area of the substrate,
(3a) anisotropic etching of the silicon, in particular with a dry etching process, preferably by use of reactive ion etching (RIE) and/or deep reactive ion etching (DRIE), of solid and/or hollow first structural elements that are open towards the second layer boundary, in particular of silicon, into the first area of the substrate, in particular the first boundary surface region of the main body of the ATR reflection element.

The method is further suitable using a metal-assisted chemical etching process (MACE), in particular comprising the following steps in the stated order:
(2b) formation of a thin metal layer, in particular noble metal layer, preferably a gold layer and/or silver layer, wherein the thickness of the metal layer preferably corresponds to the thickness of the transmission layer,
(3b) structuring of the metal layer, in particular by vaporization of the metal, such that sub-regions of the metal layer are removed,
(4b) anisotropic etching of the silicon, in particular by use of $HF/H_2O_2$, and subsequent removal of the metal layer, so forming solid and/or hollow first structural elements that are open towards the second layer boundary, in particular of silicon, in the first area.

Further suitable is a lift-off method, in particular comprising the following steps in the stated order:
(2c) machining by use of lithography, in particular DUV lithography, of the first area of the substrate,
(3c) deposition of a material which forms the transmission layer, in particular by thermal vaporization,
(4c) removal of the coating layer, in particular wet chemical dissolution of the coating layer, so forming the solid and/or hollow first structural elements that are open towards the second layer boundary.

The latter method can also be used to produce a transmission layer with solid and/or hollow first structural elements that are open towards the second layer boundary, which is produced from a material that differs from the substrate or main body. Here, it should be specified that the standards for this material with regard to transparency can be lower than for the material of the main body. Unlike the main body, the transmission layer is very thin.

After the hollow and/or solid first structural elements, as described above, have been created, the solid and/or hollow second structural elements that are open towards the layer boundary are formed according to a second etching method, which differs from the first etching method. However, according to the disclosure it is also possible to first form the hollow second structural elements that are open towards the second layer boundary and then the hollow first structural elements that are open towards the second layer boundary and/or the solid first structural elements. Preferably, the second structural elements are formed by an, in particular wet chemical, etching method, comprising the following steps in the stated order:
(5) application of at least one coating layer, in particular photoresist layer, onto a flat second area opposite the first area, in particular the second, third and/or fourth boundary surface region
(6) machining by use of lithography of the second area of the substrate, in particular of the second, third and/or fourth boundary surface region,
(7) anisotropic etching of the silicon, in particular by use of a wet chemical etching method, preferably KOH etching, of the second area of the substrate, in particular of the second, third and/or fourth boundary surface region.

The method described with steps (1), (2a) and (3a) for forming the hollow first structural elements that are open towards the second layer boundary and/or solid first structural elements is particularly preferred. The creation of a transmission layer comprising hollow first structural elements that are open towards the second layer boundary and/or solid first structural elements is here preferably achieved through the application of at least one photoresist layer on a first flat area of the substrate, structuring the first flat area of the substrate using lithography, in particular DUV lithography, and at least one etching step with a first etching method, in particular a DRIE etching step.

Silicon is particularly suitable as material for the substrate. For silicon, lithography and structuring methods are known from semiconductor production. When anisotropic etching is used in silicon, hollow and/or solid second structural elements are created, in particular with V-shaped grooves. The angle of the flank created by anisotropic etching is determined by the crystallographic orientation of the substrate. Standard ATR reflection elements made of silicon are usually produced mechanically by cutting and polishing without a structuring step being conducted. It is also known from Schumacher et al., Appl Spectrosc. 2010, 64(9), 1022-7, that special silicon ATR reflection elements can be produced from silicon-100 wafers. The angle of the groove flanks to the planar boundary surface region of the main body is here preferably approximately 55°, in particular 54.74°. If the electromagnetic radiation is irradiated vertical to said flanks, the angle of incidence $\alpha 1$ onto the sample take-up area is preferably approximately 55°, in particular 54.74°. This large angle of incidence already facilitates the total reflection with low differences between the refractive indices involved. For the use of the ATR reflection element according to the disclosure, it has however been surprisingly shown to be advantageous to use silicon-110 wafers instead. By use of anisotropic etching, second structural elements are preferably etched into the boundary region areas for coupling and decoupling the ATR reflection element. Here, the flank angle is only approximately 35°, in particular 35.26°. An irradiation of the electromagnetic radiation along the surface normals of the flanks has a considerably smaller angle of incidence on the first layer boundary. The unwanted total reflection on the first layer boundary is prevented and then only occurs on the second layer boundary.

The present disclosure leads to a significant strengthening of the absorption signal during ATR spectroscopy and ATR infrared spectroscopy. This is a particular advantage with weakly absorbing samples or strongly diluted samples. The strengthening of the absorption signal permits shorter optical passage lengths through the ATR reflection element than with standard ATR reflection elements with the same capacity. As a result, materials can also be used to produce the ATR reflection elements that are otherwise only suitable to a limited degree due to their absorption behavior. Additionally, the ATR reflection element according to the disclosure offers a filter effect in a suitable embodiment that enables the separation of the sample into components of different geometric dimensions.

BRIEF DESCRIPTION OF THE SEVERAL VIEWS OF THE DRAWINGS

Further features and advantages of the present disclosure emerge from the description below, in which the exemplary preferred embodiments of the disclosure are explained with reference to schematic drawings, in which.

DETAILED DESCRIPTION

Figure 1:
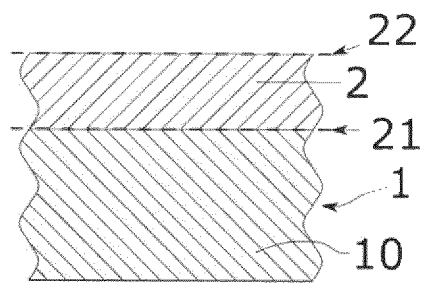
FIG. 1 shows a schematic cross-section of an embodiment of the ATR reflection element according to the present disclosure.

FIG. 1 shows the schematic side view of an embodiment of the ATR reflection element (1) according to the present disclosure. It comprises a main body (10) with a first effective refractive index to which a transmission layer (2) is adjoined via a first layer boundary (21). The transmission layer (2) can for example be formed as a porous transmission layer (the pores are not shown) and take up a fluid via a second layer boundary (22) which lies opposite the first layer boundary (21). On the second layer boundary (22), the transmission layer (2) has a second effective refractive index which is smaller than the first effective refractive index, but larger than 1. The second refractive index determines the angle at which the total reflection can occur at the boundary region to the vacuum.

Figure 2:
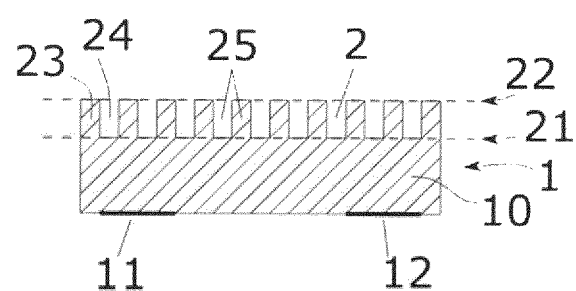
FIG. 2 shows a schematic cross-section of a further embodiment of the ATR reflection element with a transmission layer, also known as a measurement layer or SWS transmission layer, comprising solid and hollow regions.

FIG. 2 shows a further embodiment of the ATR reflection element (1) according to the disclosure. The main body (10) comprises a second boundary surface region for coupling (11) and a third boundary surface region for decoupling (12) the electromagnetic radiation, which are here arranged opposite the transmission layer (2). Via the first layer boundary (21), the transmission layer (2) adjoins the main body (10). The transmission layer (2) has alternately solid regions (23) and hollow regions (24), which in this example are formed by periodic elevations and wells. These are preferably formed as hollow first structural elements that are open towards the second layer boundary and solid first structural elements (25). Via the second layer boundary (22), a fluid can penetrate into the hollow regions (24) of the transmission layer. The hollow regions are accordingly open towards the second layer boundary.

Figure 3:
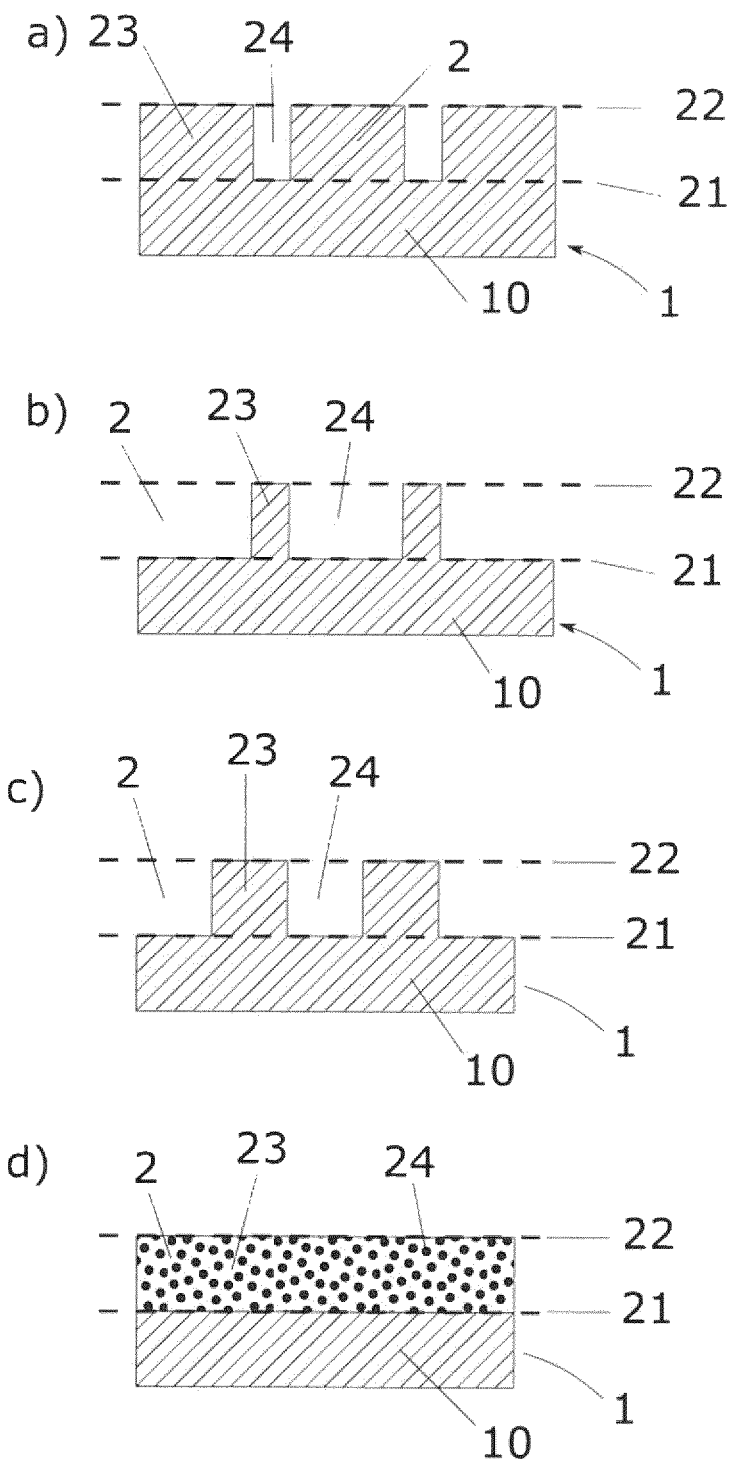
FIGS. 3a)-3d) show schematic cross-sections of embodiments of the ATR reflection element with different designs of the transmission layer.

FIGS. 3a)-3d) show, in a side view, different possible embodiments of the transmission layer (2). FIG. 3a) shows an embodiment in which there are more solid regions (23) than hollow regions (24) in the transmission layer (2). Here, the fill factor is more than 50%. FIG. 3b) shows an embodiment in which there are more hollow regions (24) than solid regions (23) in the transmission layer. Here, the fill factor is less than 50%. In FIG. 3c), solid regions (23) and hollow regions (24) take up the same space in the transmission layer. In this embodiment, the fill factor is 50%. An alternative embodiment is formed by the porous structure shown in FIG. 3d). The size and number of the hollow regions (24) designed as pores in relation to the total volume or the total surface of the cross-section of the transmission layer (2) determine the fill factor.

Figure 4:
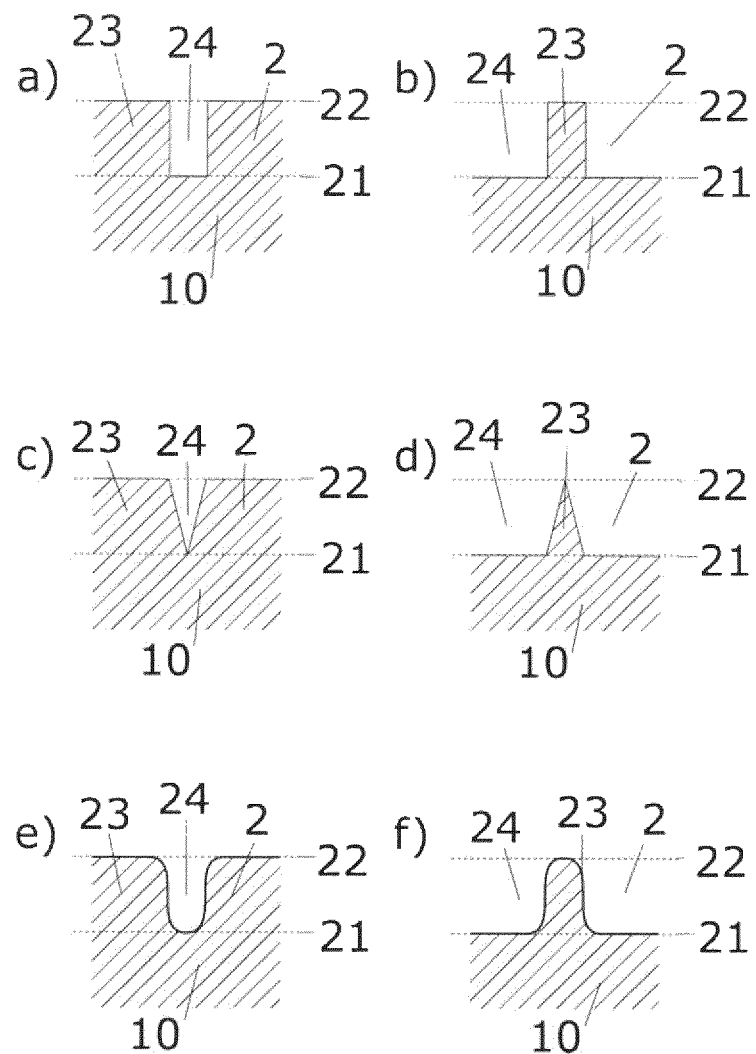
FIGS. 4a)-4f) show schematic cross-sections of designs according to the disclosure of the hollow first structural elements that are open towards the second layer boundary and/or solid first structural elements, which are formed from elevations and/or wells, and which form the solid and hollow regions of the transmission layer.

In FIGS. 4a)-4f), further possible embodiments of the first structural elements (25), which are designed as elevations and/or wells, which are formed from solid regions (23) or hollow regions (24) of the transmission layer (2), are shown in a side view. FIGS. 4a) and 4b) show embodiments with a rectangular cross-section. Here, the fill factor is constant over the entire thickness of the transmission layer (2). In FIGS. 4c) and 4d), the first structural elements (25) have a triangular cross-section. The fill factor changes over the entire thickness of the transmission layer (2). In FIGS. 4e) and 4f), the fill factor remains constant over large portions of the thickness of the transmission layer (2). Close to the first layer boundary (21) and the second layer boundary (22), the fill factor changes due to the rounded edges.

While the inclination of the flanks is 90° in designs 4a) and 4c), for design 4b) the inclination is 75°.

Figure 5:
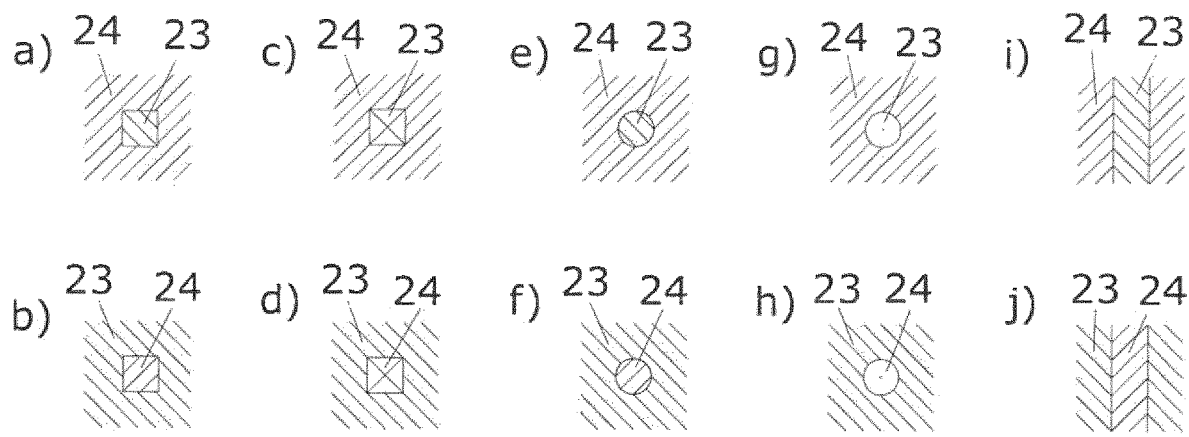
FIGS. 5a)-5j) show schematic top views onto embodiments of the hollow first structural elements that are open towards the second layer boundary and/or solid first structural elements.

FIGS. 5a)-5J0 show, in a top view, different embodiments of the solid regions (23) and the hollow regions (24) of the transmission layer. The resulting elevations (top row) and wells (bottom row) can have different forms. FIGS. 5a) and 5b) show cuboid or cube-shaped elevations and wells. FIGS. 5c) and 5d) show pyramid-shaped solid first structural elements. In FIGS. 5e) and 5f), solid cylindrical first structural elements can be seen. FIGS. 5g) and 5h) show cone-shaped first structural elements. The solid regions (23) and hollow regions (24) of the transmission layer can also be extended along one or more spatial directions parallel to the first and/or second layer boundary. As a result, longitudinal elevations and wells are created as shown in FIGS. 5i) and 5j). Even though solid and hollow regions are present, this does not mean that solid and hollow structural elements must be present. FIGS. 5a), 5c), 5e) and 5g) show only solid structural elements. The intermediate spaces are continuously connected and form a base surface. FIGS. 5b), 5d), 5f), and 5h) show only hollow structural elements. The intermediate region is elevated and forms a continuous plateau surface. In FIGS. 5i) and 5j), both hollow structural elements and solid structural elements are present.

Figure 6:
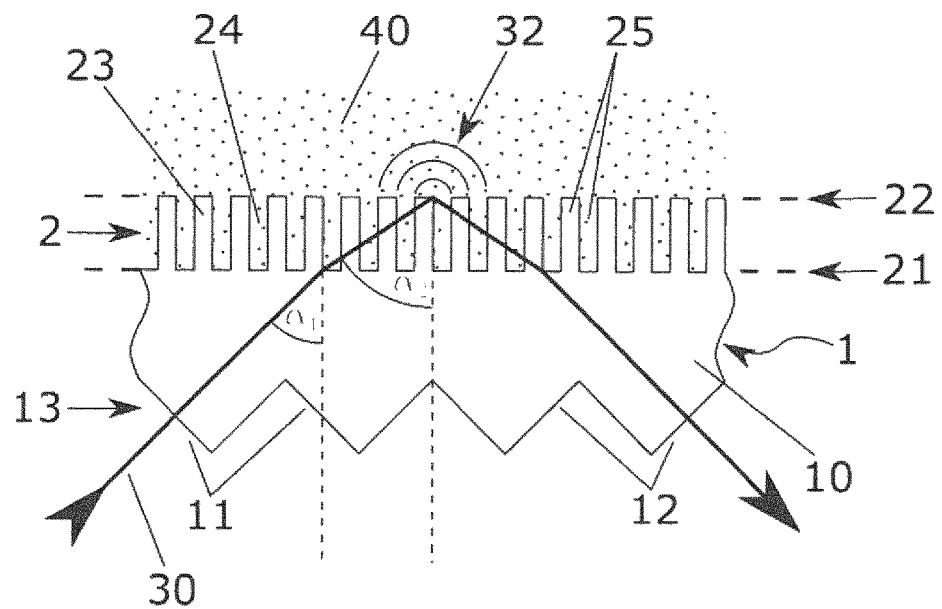
FIG. 6 shows the schematic cross-section including a possible beam passage through a single reflection element comprising second structural elements in the coupling and decoupling region and the transmission layer formed from the subwavelength structures.

FIG. 6 shows a schematic drawing of the beam passage of the measurement beam of a preferred embodiment of the ATR reflection element (1) or in a preferred embodiment of the ATR spectrometer according to the disclosure. The electromagnetic radiation (30) enters the main body (10) of the ATR reflection element (1) via the second boundary surface regions for coupling the electromagnetic radiation (11), which are formed from flanks of solid and/or hollow second structural elements (13), with a first effective refractive index $n_1$. The angle of incidence is selected in this embodiment such that the radiation impinges on the flanks of the solid and/or hollow structural elements at right angles. Experience has shown that thus, the share of the electromagnetic radiation already reflected when entering the ATR reflection element is reduced, so that a potentially larger share of the electromagnetic radiation is available for the actual absorption measurement of the analytes. The electromagnetic radiation (30) runs through the main body (10) of the ATR reflection element (1) and impinges onto the first layer boundary (21) at an angle of incidence $\alpha 1$ compared to the perpendicular. The transmission layer (2) consists of alternate solid and/or hollow first structural elements that are open towards the second layer boundary (25) formed from solid regions (23) and hollow regions (24) in the subwavelength range of the electromagnetic radiation used. The fluid to be tested, in particular including the analytes (40), penetrates through the second layer boundary (22) into the hollow regions (24) of the transmission layer (2). In the embodiment shown, the fill factor is constant over the entire thickness of the transmission layer (2). The angle of incidence $\alpha 1$ is selected such that on the first layer boundary (21), no total reflection occurs. The electromagnetic radiation (30) is broken away from the perpendicular when entering the transmission layer (2). The electromagnetic radiation (30) passes through the transmission layer (2) and here also crosses the hollow regions (24) of the transmission layer (2) filled with fluid and/or analytes (40). The electromagnetic radiation (30) impinges on the second layer boundary (22) at an angle $\alpha 2 > \alpha 1$. On this second layer boundary (22) the electromagnetic radiation (30) is totally reflected between the effective transmission layer (2) and the fluid and/or analytes (40). Here, evanescent waves (32) penetrate into the fluid and/or the analytes. The total reflected electromagnetic radiation (30) again passes through the transmission layer (2). At the first layer boundary (21), the electromagnetic radiation (30) again enters into the main body (10) of the ATR reflection element (1). In the embodiment shown here, the electromagnetic radiation (30) is then decoupled from the ATR reflection element via the third boundary surface regions for decoupling the electromagnetic radiation (12), also formed from flanks of the solid and/or hollow second structural elements (13). This is thus a single reflection element.

Figure 7:
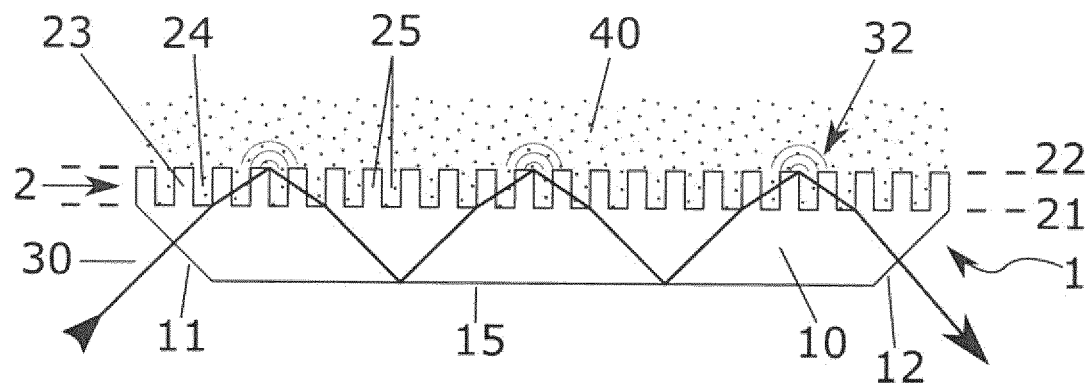
FIG. 7 shows a schematic cross-section including the beam passage through a multiple reflection element according to the present disclosure.

In FIG. 7, an embodiment as a multiple reflection element is shown schematically. On the boundary surface region for coupling the electromagnetic radiation (11), the electromagnetic radiation (30) is coupled into the main body (10) of the ATR reflection element (1). The electromagnetic radiation then enters into the transmission layer (2) via the first layer boundary (21), wherein it undergoes refraction. The electromagnetic radiation (30) passes through the transmission layer (2) until it impinges on the second layer boundary (22) to the fluid or to the analytes (40). When passing through the transmission layer (2), the electromagnetic radiation (30) transmits via the fluid (40) that has penetrated into the hollow regions (24) of the transmission layer (2). On the second layer boundary (22), there is a total reflection, wherein evanescent waves (32) penetrate into the fluid. Subsequently, the electromagnetic radiation (30) again passes through the transmission layer (2) and is refracted at the first layer boundary (21) into the main body (10). On the side of the main body (15) opposite the transmission layer (2), the electromagnetic radiation (30) is again reflected towards the transmission layer (2). The electromagnetic radiation (30) again passes through the transmission layer (2) and is totally reflected on the second layer boundary (22). This procedure can be conducted once or multiple times until the electromagnetic radiation (30) is finally decoupled from the main body (10) on the boundary surface region for decoupling the electromagnetic radiation (12).

Figure 8:
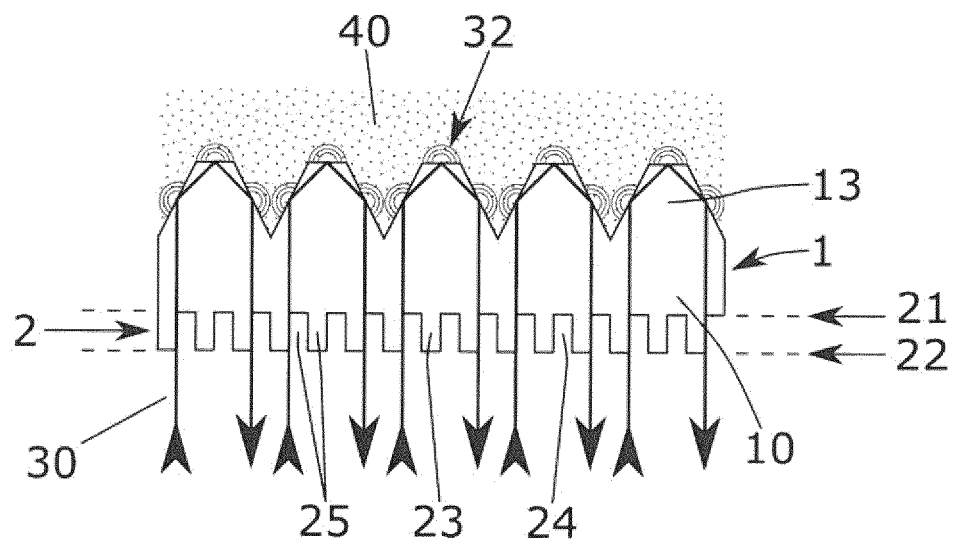
FIG. 8 shows a schematic cross-section through an embodiment according to the present disclosure as a triple reflection element, wherein the SWS transmission layer in this embodiment forms the regions for coupling and decoupling the electromagnetic radiation and the hollow and/or solid second structural elements form the sample take-up area.

FIG. 8 shows a schematic drawing of an embodiment of the ATR reflection element according to the disclosure as a triple reflection element. Here, the transmission layer (2) forms the regions for coupling and decoupling the electromagnetic radiation (30) and the solid and/or hollow second structural elements (13) form the sample take-up area. The electromagnetic radiation (30) penetrates into the transmission layer (2) via the second layer boundary (22). The transmission layer acts as an anti-reflection layer, so that the portion of electromagnetic radiation (30) reflected when entering the ATR reflection element (1) is considerably reduced compared to irradiation onto a flat boundary region (moth-eye effect). The electromagnetic radiation (30) enters into the main body (10) of the ATR reflection element (1) and is totally reflected once respectively on the three sides adjoining the fluid and/or the analytes (40) of the trapezoid-profile solid and/or hollow second structural elements (13), wherein evanescent waves (32) penetrate into the fluid and/or the analytes (40). The electromagnetic radiation (30) is subsequently again decoupled from the ATR reflection element (1) via the transmission layer (2).

Figure 9:
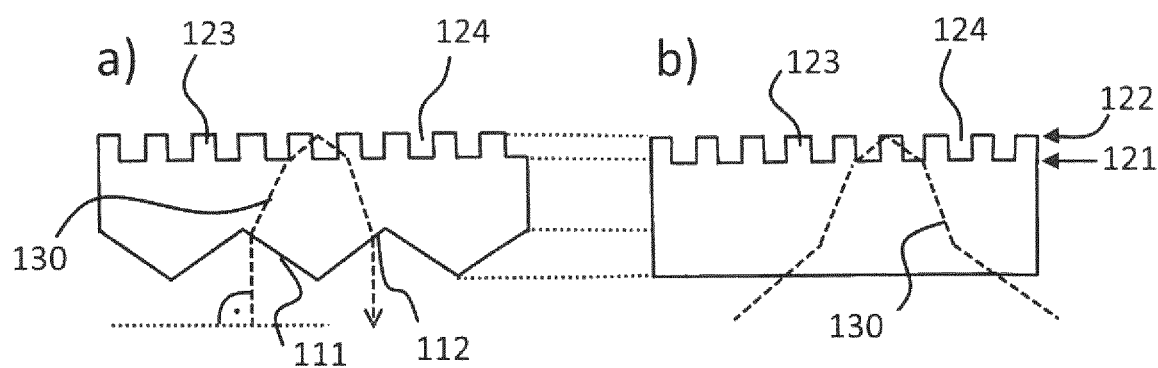
FIGS. 9a) and 9b) show schematic cross-sections through a single reflection element according to the present disclosure including a further possible beam passage, comprising hollow and/or solid second structural elements in the coupling and decoupling region and the transmission layer formed from the subwavelength structures.

FIGS. 9a) and 9b) show a schematic drawing of the beam passage of the measurement beam of an embodiment of the ATR reflection element, wherein the electromagnetic radiation (130) enters into the main bodies of the ATR reflection element with a first effective refractive index $n_1$ via the second boundary surface regions for coupling the electromagnetic radiation (111), which are formed from flanks of second structural elements. The cross-section view 9a) shows a cross-section that is arranged orthogonally to the V-shaped grooves on the underside. The cross-section view 9b) shows a cross-section of the same embodiment rotated by 90°, wherein said cross-section occurs parallel to the V-shaped grooves on the underside. The transmission layer is limited in both cross-section views by the first and second layer boundary (121, 122). The transmission layer is formed from columns (123) and the intermediate spaces (124) for taking up the fluid between the columns. With regard to the cross-section view 9a), the light beam is irradiated orthogonally to the said layer boundaries, and is refracted when entering the main body. In the cross-section, a plane that runs parallel to the second layer boundary is shown as a broken line, wherein the light beam is arranged orthogonally to it. This does not apply, however, to the cross-section view 9b), wherein here, the light beam penetrates into the crystal at an acute angle and is refracted. The irradiation vector of the light thus lies on a plane that is oriented orthogonally to the first and/or second layer boundary and parallel to the V-shaped grooves. Ultimately, the light is irradiated along the V-shaped grooves, so that the arms can be illuminated evenly. The goal is to secure an even angle of incidence in the cross-section view 9b). It has been shown that this is linked to improved measuring results. The angle of incidence is however not selected in this embodiment such that the radiation impinges on the flanks of the solid or the above-mentioned hollow second structural elements at right-angles. The diffraction behavior and the total reflection on the first and second layer boundary have already been described in connection with the other figures, in particular FIG. 6, and occur here analogously.

The features of the present disclosure in the above description, in the claims and in the drawings can be essential both individually and in any combination required for the realisation of the invention in its different embodiments.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An attenuated total reflection (ATR) element, comprising: a main body with a first effective refractive index $n_1$, a transmission layer, which has a first layer boundary and an opposite second layer boundary, wherein the transmission layer is designed and configured to take up a fluid by way of the second layer boundary, wherein the transmission layer adjoins the main body or a first boundary surface region of the main body, wherein the boundary between transmission layer and the main body is formed by the first layer boundary, wherein the transmission layer has a second effective refractive index $n_2$ at the second layer boundary, wherein the first effective refractive index $n_1$ is greater than the second effective refractive index $n_2$ and the second effective refractive index $n_2$ is greater than 1, and wherein the first effective refractive index $n_1$ and the second effective refractive index $n_2$ are each determined in a vacuum at 25° C. at the IR wavelength $\lambda_{ATR}$, wherein $\lambda_{ATR}$ is selected from a wavelength range from 2 μm to 20 μm.

2. The ATR reflection element according to claim 1, wherein
the ATR reflection element has at least one second boundary surface region of the main body for coupling electromagnetic radiation and at least one third boundary surface region of the main body for decoupling electromagnetic radiation.

3. The ATR reflection element according to claim 1, wherein
the transmission layer comprises a plurality of solid first structural elements and/or hollow first structural elements open towards the second layer boundary.

4. The ATR reflection element according to claim 3, wherein
the hollow and/or solid first structural elements of the transmission layer are arranged periodically or aperiodically, such that at least one cross-sectional area is arranged between the first and second layer boundaries, wherein said at least one cross-sectional area comprises similarly configured, solid regions delimited from one another arranged periodically or aperiodically.

5. The ATR reflection element according to claim 3, wherein
the first and the second layer boundaries are arranged in parallel, wherein the solid first structural elements and/or the hollow first structural elements open towards the second layer boundary extend from the first to the second layer boundary.

6. The ATR reflection element according to claim 3, wherein
at least one lattice constant of the periodically arranged solid and/or hollow first structural elements open towards the second layer boundary and/or the average spacing of the periodically or aperiodically arranged solid and/or hollow first structural elements open towards the second layer boundary fulfil(s) the condition (Ia)

$$p_{max} < \frac{500 \ \mu m}{n_1}$$

wherein $n_1$ is the first effective refractive index and $p_{max}$ is the value of the at least one lattice constant and/or average spacing.

7. The ATR reflection element according to claim 3, wherein
the hollow first structural elements open towards the second layer boundary are formed as wells and/or the solid first structural elements are formed as raised portions.

8. The ATR reflection element according to claim 3, wherein
the hollow first structural elements open towards the second layer boundary and/or the solid first structural elements have at least one lattice constant and/or an average spacing in a range from 0.1 to 4 μm.

9. The ATR reflection element according to claim 3, wherein
the solid first structural elements have a fill factor in the range from 1 to 85 vol. %.

10. The ATR reflection element according to claim 3, wherein the solid first structural elements have a height and/or the hollow first structural elements open towards the second layer boundary have a depth, determined from the first layer boundary towards the second layer boundary, in a range from 0.5 to 50 µm, and/or wherein the distance between the first and second layer boundaries is in a range from 0.5 to 50 µm, and/or wherein the distance between the first and second layer boundaries corresponds to a height of the solid first structural elements or a depth of the hollow first structural elements open towards the second layer boundary.

11. The ATR reflection element according to claim 3, wherein the hollow first structural elements open towards the second layer boundary and/or the solid first structural elements each have at least one identical cross-sectional area.

12. The ATR reflection element according to claim 2, wherein the second and/or third boundary surface region has solid and/or open hollow second structural elements, and/or wherein the ATR reflection element comprises at least one fourth boundary surface region which has solid and/or open hollow second structural elements.

13. The ATR reflection element according to claim 12, wherein the main body and the transmission layer consist of one material and/or wherein the main body and the solid second structural elements consist of one material.

14. The ATR reflection element according to claim 1, wherein the first effective refractive index $n_1$ and the second effective refractive index $n_2$ are each determined in a vacuum at 25° C. with electromagnetic radiation of an IR wavelength of 15 µm.

15. The ATR reflection element according to claim 1, wherein the ATR reflection element and/or the main body comprises or constitutes a crystal, and/or wherein the ATR reflection element is formed in part or completely of silicon and/or germanium and/or zinc selenide and/or diamond and/or thallium bromide-iodide and/or amorphous material transmitting infrared radiation (AMTIR).

16. The ATR reflection element according to claim 12, wherein the boundary surface region having second structural elements is not arranged on the side of the ATR reflection element on which the transmission layer is present, and/or wherein the boundary surface region having second structural elements is arranged on the side the ATR reflection element opposite to the transmission layer.

17. The ATR reflection element according to claim 1, wherein the ATR reflection element is designed as a single reflection element or multiple reflection element.

18. The ATR reflection element according claim 12, wherein the average spacing between respectively adjacent solid second structural elements and/or the average spacing between the respectively adjacent hollow second structural elements is greater than the average spacing between respectively adjacent solid first structural elements and/or the average spacing between the respectively adjacent hollow first structural elements open towards the second layer boundary, and/or wherein the solid and/or the hollow first and second structural elements are arranged periodically.

19. The ATR reflection element according to claim 12, wherein the solid and/or the hollow second structural elements each have an average spacing and/or at least one lattice constant in a range from 30 to 3000 µm, and/or wherein the average spacings and/or one or a plurality of the lattice constants of the solid and/or hollow first structural elements is/are each smaller by at least a factor of 5 than the respective average spacings and/or one or a plurality of the lattice constants of the solid and/or hollow second structural elements.

20. The ATR reflection element according to claim 12, wherein the hollow second structural elements comprise or constitute V-shaped grooves.

21. The ATR reflection element according to claim 20, wherein the V-shaped grooves have an average or absolute depth in a range from 15 to 1517 µm.

22. The ATR reflection element according to claim 20, wherein the boundary surface regions of the main body provided with second structural elements have a mask region of less than 50% of said boundary surface regions.

23. The ATR reflection element according to claim 1, obtained or obtainable using a manufacturing method comprising the provision of a plane-parallel substrate, and the formation of a transmission layer containing first structural elements by (1) application of at least one coating layer onto a flat first area of the substrate, and by a subsequent first etching method comprising:

(2a) machining by use of lithography of the first area of the substrate, (3a) anisotropic etching of the first structural elements into the first area of the substrate, and by forming second structural elements by use of a second etching method comprising:

(5) application of at least one coating layer onto a flat second area opposite the first area, (6) machining by use of lithography of the second area of the substrate (7) anisotropic etching of the second area of the substrate, wherein the second structural elements are formed before or after the first structural elements.

24. The ATR reflection element according to claim 23, wherein the main body and/or the transmission layer and/or the substrate provided according to claim 23 comprises or constitutes a silicon substrate, and/or wherein the transmission layer is provided by a dry etching method and the second structural elements are provided by a wet etching method.

25. The ATR reflection element according to claim 3, wherein the first structural elements form a subwavelength structure with regard to the wavelength $\lambda_{ATR}$ and/or wherein the transmission layer comprises a subwavelength structure with regard to the wavelength $\lambda_{ATR}$.

26. An ATR spectrometer, comprising:

a light source, a detector, optical elements, and at least one ATR reflection element according to claim 1.

27. The ATR spectrometer according to claim 26, wherein,
in the case of generic use of the ATR spectrometer, the second layer boundary of the transmission layer comprises or constitutes a sample take-up area, or
wherein a boundary surface region comprising or formed of second structural elements comprises or constitutes a sample take-up area.

28. The ATR spectrometer according to claim 26, wherein the ATR reflection element has at least one second boundary surface region of the main body for coupling electromagnetic radiation and at least one third boundary surface region of the main body for decoupling electromagnetic radiation, and
wherein at least one boundary surface region, which comprises second structural elements, constitutes the second and/or third boundary surface region for coupling and/or decoupling the electromagnetic radiation, wherein the light source is arranged such that electromagnetic radiation is coupled through the second boundary surface region and decoupled through the third boundary surface region.

29. The ATR spectrometer according to claim 26, wherein the transmission layer comprises a plurality of solid first structural elements and/or hollow first structural elements open towards the second layer boundary and at least one lattice constant and/or the average spacing of the hollow first structural elements open towards the second layer boundary and/or the solid first structural elements fulfil(s) the relationship (II)

$$p_{max} < \frac{\lambda_{ATR2}}{n_{1b}(1 + \sin\alpha_1)}$$

wherein $n_{1b}$ constitutes a third effective refractive index of the main body of the ATR reflection element with electromagnetic radiation of the wavelength $\lambda_{ATR2}$ and at 25° C. in a vacuum, and $\alpha_1$ denotes the angle of incidence at the first layer boundary predetermined by the arrangement of the light source,
wherein $p_{max}$ is the value of the at least one lattice constant and/or average spacing and $\lambda_{ATR2}$ is the wavelength 15 µm.

30. An ATR spectroscopy method, comprising:
introducing a fluid into the transmission layer of an ATR reflection element according to claim 1,
partly or completely vaporizing the fluid,
coupling a beam of light into and out of the ATR reflection element, wherein this beam of light impinges at least once, between coupling and decoupling;
on the first layer boundary and penetrates into the transmission layer delimited by this layer boundary and capable of fluid take-up, wherein the beam of light undergoes refraction at the first layer boundary and, on passage through the transmission layer, undergoes transmission by the fluid taken up into the transmission layer,
and on the fluid-permeable second layer boundary, wherein the beam of light undergoes total reflection at the second layer boundary, wherein the beam of light, on further passage through the transmission layer, again undergoes transmission by the fluid taken up into the transmission layer,
wherein, on transmission, the beam of light also undergoes absorption by the fluid,
wherein, after at least one instance of total reflection at the second layer boundary, the beam of light once again enters the main body of the ATR reflection element at the first layer boundary,
and wherein the beam of light is attenuated by the absorption and is detected with a detector after emerging from the ATR reflection element.

31. The ATR spectroscopy method according to claim 30, wherein
the fluid is dispensed onto a sample take-up area of the ATR reflection element and penetrates into the transmission layer.

32. A method for producing an ATR reflection element according to claim 1, comprising:
providing a plane-parallel substrate,
forming a transmission layer containing first structural elements by
(1) applying at least one coating layer onto a flat first area of the substrate,
and by a subsequent first etching method comprising:
(2a) machining by use of lithography of the first area of the substrate,
(3a) anisotropic etching of first structural elements into the first area of the substrate,
or by a subsequent metal-assisted chemical etching (MACE) method comprising:
(2b) forming a thin metal layer,
(3b) structuring of the metal layer such that sub-regions of the metal layer are removed,
(4b) anisotropic etching and subsequent removal of the metal layer, so forming first structural elements in the first area,
or by a subsequent lift-off method comprising:
(2c) machining by use of lithography of the first area of the substrate,
(3c) depositing a material which forms the transmission layer,
(4c) removing the coating layer so forming the first structural elements.

33. The method according to claim 32, further comprising:
forming second structural elements by a second etching method, comprising:
(5) applying at least one coating layer onto a flat second area opposite the first area,
(6) machining by use of lithography of the second area of the substrate,
(7) anisotropic etching of the second area of the substrate,
wherein the second structural elements are formed before or after the first structural elements.

34. The method according to claim 32, wherein
the substrate provided comprises or constitutes a silicon substrate,
and/or wherein the transmission layer is provided by a dry etching method and the second structural elements by a wet etching method.

* * * * *

UNITED STATES PATENT AND TRADEMARK OFFICE
CERTIFICATE OF CORRECTION

PATENT NO. : 10,585,040 B2
APPLICATION NO. : 15/760005
DATED : March 10, 2020
INVENTOR(S) : Lorenz Sykora Page 1 of 1

It is certified that error appears in the above-identified patent and that said Letters Patent is hereby corrected as shown below:

In the Claims

Column 29, Claim 29, Line 41:
"electromagnetic radiation of the wavelength $\lambda_{ATR2}$ and"
Should read:
--electromagnetic radiation of the wavelength $\lambda_{ATR2}$--.

Column 30, Claim 32, Line 21:
"providing a plane-parallel substrate,"
Should read:
--providing a plane-parallel substrate, and--.

Signed and Sealed this
First Day of September, 2020

Andrei Iancu
*Director of the United States Patent and Trademark Office*